United States Patent [19]

Meilland

[11] Plant 4,705

[45] May 5, 1981

[54] ROSE PLANT-MEIBIRANDA VARIETY

[75] Inventor: Marie L. Meilland, Antibes, France

[73] Assignee: The Conard-Pyle Company, West Grove, Pa.

[21] Appl. No.: 76,311

[22] Filed: Sep. 17, 1979

[30] Foreign Application Priority Data

Oct. 24, 1978 [MA] Morocco ..... PV18433

[51] Int. Cl.[3] ..... A01H 5/00

[52] U.S. Cl. ..... Plt./11

[58] Field of Search ..... Plt./11

*Primary Examiner*—Robert E. Bagwill

*Assistant Examiner*—James R. Feyrer

*Attorney, Agent, or Firm*—Burns, Doane, Swecker & Mathis

[57] ABSTRACT

A new and distinct variety of Hybrid Tea rose plant is provided which has double bicolored flowers and very vigorous vegetation. The petals are mimosa yellow in the center and have edges which are poppy red on the inside and red currant red on the outside. The seed parent of the new variety was the variety Ester Ofarim and the pollen parent was formed by the crossing of the variety Super Star and the variety Flirt.

13 Drawing Figures

SUMMARY OF THE INVENTION

The object of the present invention is to provide a new and distinctive variety of rose plant of the Hybrid Tea Class having double flowers with petals which are bicolored on both the inside and on the outside. The inside of the petals is poppy red on the edge and mimosa yellow in the center, and the outside of the petals is red currant red on the edge and mimosa yellow in the center.

In view of these characteristics the new variety meets the needs of the horticultural industry for all uses, and especially for the production of cut flowers in greenhouses.

The seed parent of the new variety was the variety Ester Ofarim and the pollen parent was the product of the crossing of the variety Super Star and the variety Flirt (U.S. Plant Pat. No. 1,122). This parentage of the new variety may be expressed as follows:

Ester Ofarim × [Super Star × Flirt].

The seeds resulting from the above pollination were sown and 70 small plants were obtained which were physically and biologically different from each other. Selective study resulted in the identification and preservation of the new variety. Extensive testing has confirmed the behavior and productivity of the new variety. The results were conclusive and have documented the creation of an important new rose variety suitable for commercial exploitation which is particularly useful for the production of cut flowers.

The characteristics and properties of this new variety, obtained as indicated above are strictly transmissible by agamic means, also called "asexual", i.e., by means of vegetative propagation, in particular by grafting an eye. The rose plant of the new variety has been designated the Meibiranda variety.

BRIEF DESCRIPTION OF THE PHOTOGRAPH

The accompanying photograph shows as nearly true as it is reasonably possible to make the same in a color illustration of this character, typical specimens of the cut flowers and foliage of the present variety, illustrated in:

FIG. 1—a portion of a young stem;

FIG. 2—a specimen of a bud at the opening of the sepals;

FIG. 3—a specimen of a bud at the first opening of the petals;

FIG. 4—a specimen of a flower in the course of opening;

FIG. 5—a specimen of an open flower;

FIG. 6—a specimen of a floral receptacle showing the stamens and stigmas—plan view;

FIG. 7—a specimen of a floral receptacle showing the arrangement of the styles (stamens removed);

FIG. 8—a portion of a floral stem;

FIG. 9—a portion of a main branch;

FIG. 10—a specimen of a 3-foliole leaf—upper surface;

FIG. 11—a specimen of a 5-foliole leaf—under surface;

FIG. 12—a specimen of a 7-foliole leaf—upper surface; and

FIG. 13—a specimen of an open flower—plan view.

DETAILED DESCRIPTION OF THE DISCLOSURE

Figures 1, 2, 3, 4, 5, 6, 7, 8, 9, 10, 11, 12, 13:
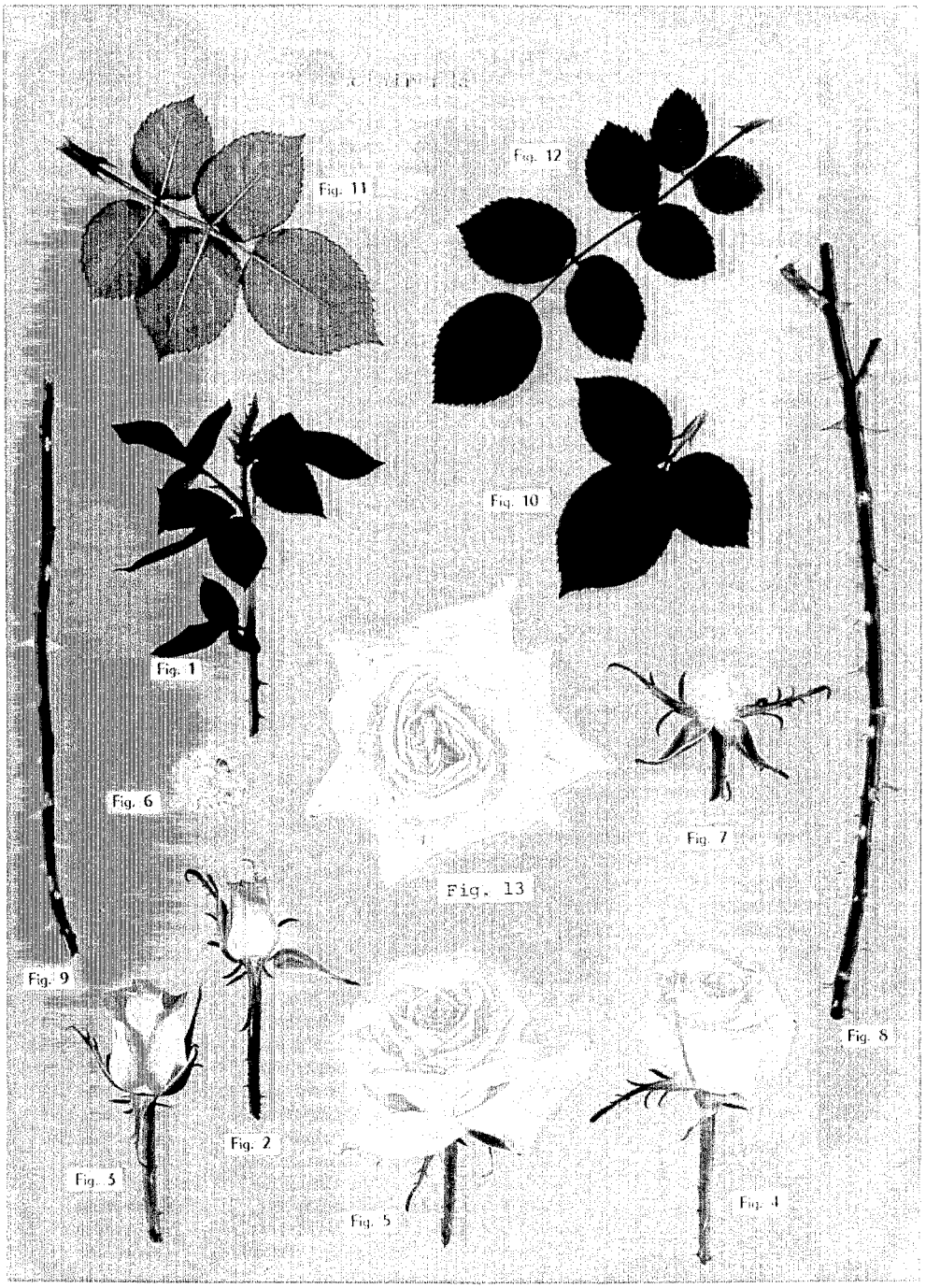

The plant described was grown under glass at Cap d' Antibes, Alpes Maritimes, France.

The chart used in the identification of the colors is that of the Royal Horticultural Society (R.H.S. Color Chart). The terminology preceding the numbered references proper to this chart has been to designate, in common terms, the corresponding colors.

Class: Hybrid tea

Plant:

*Height.*—1.25 to 1.45 meters. Stems commonly can be cut which are 40 to 60 centimeters in length.

*Habit.*—Straight.

Branches:

*Color.*—Young stems: before the bud is formed, the young stems are reddish violet when facing the sun, and light green when facing the shade (common terms). The first leaves also are reddish violet. Mature wood: average green 137/B (green group).

*Thorns.*—Shape: Upper edge: straight. Under edge: concave. Base: elliptical. Size: fairly thick. Quantity: fairly numerous. Color—on young stems: reddish violet. On mature wood: light green then havana brown (common terms).

Leaves:

*Stipules.*—Adnate, pectinated, average length and narrow.

*Petioles.*—Inner surface: light green groove (reddish violet edge on young leaves), glandular edges. Outer surface: light green, maculated reddish violet on young leaves, bears numerous hooked and acicular thorns.

*Folioles.*—Number: 3 to 5, also 7. Shape: oval, largely rounded and symmetrical base, large and symmetrical tip. Denticulation: coarse. General effect: generally semi-dull, relatively large and fairly dense.

*Color.*—Young foliage: Upper surface: yellowish green 147/A (yellow green group) largely suffused reddish violet, teeth reddish violet. Under surface: light green 191/B (greyed green group) more or less largely suffused reddish violet. Adult foliage: Upper surface: average green 147/A (yellow green group). Under surface: light green 191/B (greyed green group).

Inflorescence:

*Number of flowers.*—Generally one flower per stem.

*Peduncle.*—Fairly long, 9 to 10 centimeters on average, erect, rigid, light green, many aciculate.

*Sepals.*—Tomentous and whitish on inside, yellow green and smooth on outside, may be largely furnished with appendages, narrow and slim tip.

*Bud.*—Shape: slim at tip, base is rounded. Length: 40 millimeters outside the calyx, width 25 millimeters. Size: average. Color: when opening: outside: the edges of the petal are red currant red 47/A (red group), and the central part is chartreuse yellow 1/C (green yellow group).

*Flower.*—Form: first a raised center, petals well imbricated, then it opens to a cup-shaped form, double flower. Diameter: 12 to 13 centimeters. Color: When opening: inside: light red 42/A (red group) on the edges, going from mimosa yellow 8/B (yellow group) suffused with red. The median groove may be slightly tomentous and whitish. Yellow unguis. Outside: red currant red 47/A (red group) on the edges going from mimosa yellow 8/C (yellow group), slightly greenish on the median groove. Yellow unguis. During the course of opening fully: Inside: poppy red 43/C (red group) on the edges, going to mimosa yellow 8/C (yellow group) in the center. Yellow unguis. Outside: red currant red 47/B (red group) on the edges, going to mimosa yellow 8/D (yellow group) in the center. Yellow unguis. When fully open: Inside: bengal pink 61/D (red purple group) on the edges, going from yellowish white 158/C (yellow white group) in the center. Yellow unguis. Outside: bengal pink 61/D (red purple group) on the edges, going from yellowish white 158/D (yellow white group) in the center. Yellow unguis. Fragrance: light. Lasting quality: good on the plant as well as when cut. Corolla: Petals: Texture: firm, very much rounded, the lateral edges are reflexed. Shape: the first petals may show a median groove more or less pronounced. The petals in the center may be badly shaped. Number: approximately 35 to 40. Stripping of petals: the petals drop off cleanly. Stamens: Number: 50 on an average. Anthers: normal, yellow, they reach above the level of the stigmas. Filaments: average length and yellow from base to tip. Pistils: Number: 100 on an average. Stigmas: pale yellow. Styles: short, they are whitish and tomentous at the base, light purple at tip. Receptacle: light green, smooth, it is narrow and in the shape of a funnel.

Development:

*Vegetation.*—Vigorous.

*Blossoming.*—Continuous under glass.

*Resistance to diseases.*—Good.

I claim:

1. A new and distinct variety of Hybrid Tea rose plant of vegetative reproduction, as described and illustrated, characterized by the fact that:

from the physical point of view the plant with green adult wood is erect, forms double flowers which are bicolored with the inside of the petals being poppy red on the edge and mimosa yellow in the center, and the outside of the petals being red currant red on the edge and mimosa yellow in the center, the petals are largely rounded with their lateral edges reflexed, and frequently exhibit a pronounced median groove; and from the biological point of view the rose plant is of very vigorous vegetation, exhibits nearly continuous flowering under glass, and forms flowers of long duration both on and off the plant.

* * * * *